United States Patent [19]

Musser et al.

[11] Patent Number: 4,528,392

[45] Date of Patent: Jul. 9, 1985

[54] AROMATIC COMPOUNDS AS ANTIALLERGIC AGENTS

[75] Inventors: John H. Musser, Malvern; Kenneth L. Kees, West Chester, both of Pa.

[73] Assignee: American Home Products Corporation, New York, N.Y.

[21] Appl. No.: 601,521

[22] Filed: Apr. 18, 1984

[51] Int. Cl.³ .................. C07C 101/44; C07C 83/10; C07C 153/023; C07C 153/03
[52] U.S. Cl. .................. 560/43; 260/239 BF; 260/453 RW; 260/455 R; 260/500.5 H; 260/502.6; 546/216; 548/531; 548/534; 560/9; 562/426; 562/452; 562/454; 562/455; 562/456; 562/457; 564/162; 564/163; 564/167
[58] Field of Search .............. 560/43, 9, 17; 562/455, 562/454, 457, 426, 431, 452; 260/455 R, 502.6, 500.5 H, 453 RW; 564/164, 74, 77, 163, 167

[56] References Cited

U.S. PATENT DOCUMENTS

| | | | |
|---|---|---|---|
| 3,254,108 | 5/1966 | Maggiulli et al. | 560/43 |
| 3,511,804 | 5/1970 | Duennenberger et al. | 560/43 |
| 3,962,305 | 6/1976 | Pallos | 260/455 R |
| 4,036,837 | 7/1977 | Sellstedt et al. | 560/43 |
| 4,069,343 | 1/1978 | Sellstedt et al. | 560/43 |
| 4,162,988 | 7/1979 | Maze et al. | 260/455 R |
| 4,177,198 | 12/1979 | Bohen | 260/455 R |
| 4,296,129 | 10/1981 | Kadin | 424/309 |

Primary Examiner—Natalie Trousof
Assistant Examiner—Bruce D. Gray
Attorney, Agent, or Firm—George Tarnowski

[57] ABSTRACT

There are disclosed compounds of the formula

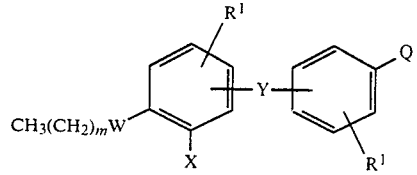

wherein
X is $OR^2$, $SR^2$, $N(R^2)_2$ or halo;
W is —CH$_2$—,

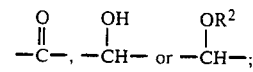

Y is —CH$_2$O—, —OCH$_2$—, —CH$_2$S—, —SCH$_2$—,

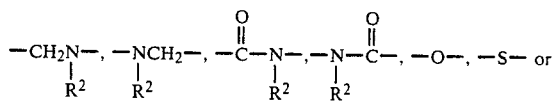

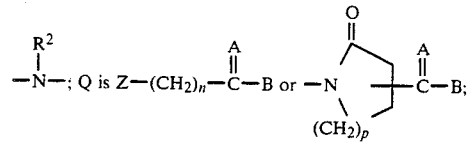

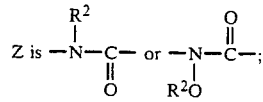

m is 0-6;
n is 0-6;
p is 1-3;
A is O or S;
B is $OR^2$, $SR^2$ or $N(R^2)_2$;
$R^1$ is hydrogen, loweralkyl, loweralkoxy or halo;
$R^2$ is hydrogen or loweralkyl;

and the pharmaceutically acceptable salts thereof, and their use in the treatment of leukotriene-mediated naso-bronchial obstructive airpassageway conditions, such as allergic rhinitis, allergic bronchial asthma and the like.

17 Claims, No Drawings

AROMATIC COMPOUNDS AS ANTIALLERGIC AGENTS

This invention relates to novel aromatic compounds possessing lipoxygenase inhibitory and slow-reacting substance of anaphylaxis (SRS-A) antagonist activity which are useful as anti-inflammatory and antiallergic agents.

It is known that arachidonic acid (AA) is metabolized in mammals by two distinct pathways. The metabolism of arachidonic acid by cyclooxygenase enzymes results in the production of prostaglandins and thromboxanes. The physiological activity of these AA metabolites has been amply elucidated in recent years. The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., *J. Immun.* 215, 115–118 (1980); *Biochem. Biophys. Res. Commun.* 93, 1121–1126 (1980)].

The significance of these leukotrienes is that a great deal of evidence is accumulating showing that leukotrienes participate in inflammatory reactions, exhibit chemotactic, activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature* 288, 484–486 (1980)], and another leukotriene, $LTB_4$, is a powerful chemotactic factor for leukocytes [see A. W. Ford-Hutchinson, *J. Roy. Soc. Med.*, 74, 831–833 (1981)]. The activity of leukotrienes and slow-reacting substances (SRS's) as mediators of inflammation and hypersensitivity is extensively reviewed in Bailey and Casey, *Ann. Reports Med. Chem.*, 17, 203–217 (1982).

The biological activity of the leukotrienes and SRS's, and of lipoxygenase as the enzyme leading to the metabolism of AA to leukotrienes, indicates that a rational approach to drug therapy to prevent, remove or ameliorate the symptoms of allergies, anaphylaxis, asthma and inflammation must focus on either blocking the release of mediators of these conditions or to anatagonize their effects. Thus, compounds which inhibit the biological effects of the leukotrienes and SRS's and/or which control the biosynthesis of these substances, as by inhibiting lipoxygenase, are considered to be of value in treating such conditions as allergic bronchial asthma, allergic rhinitis, as well as in other immediate hypersensitivity reactions.

The invention provides novel compounds of the formula

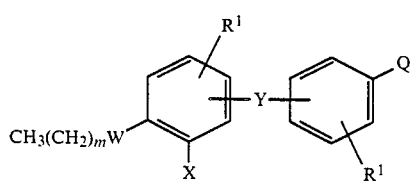

wherein

X is $OR^2, SR^2, N(R^2)_2$ or halo;

W is $-CH_2-$,

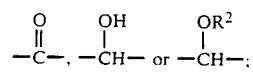

Y is $-CH_2O-$, $-OCH_2-$, $-CH_2S-$, $-SCH_2-$,

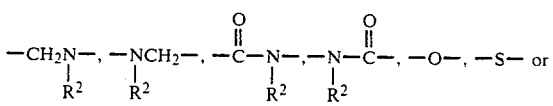

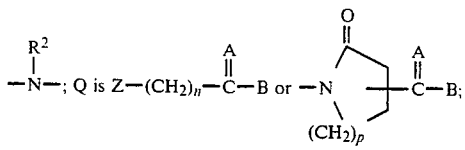

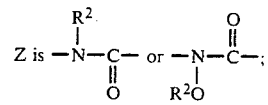

m is 0–6;
n is 0–6;
p is 1–3;
A is O or S;
B is $OR^2, SR^2$ or $N(R^2)_2$;
$R^1$ is hydrogen, loweralkyl, loweralkoxy or halo;
$R^2$ is hydrogen or loweralkyl;
and the pharmaceutically acceptable salts thereof.

The term "halo" refers to fluoro, chloro, and bromo. The terms "loweralkyl" and "loweralkoxy" refer to moieties having 1–6 carbon atoms in the carbon chain.

The compounds of the invention can be prepared in a number of ways. In those instances in which the side chain is

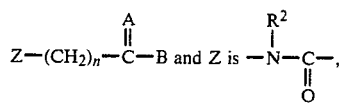

the compounds can be prepared by the reaction of an appropriate aniline derivative with the halide of an appropriate derivative of a carboxy or thiocarboxyalkanoyl as follows:

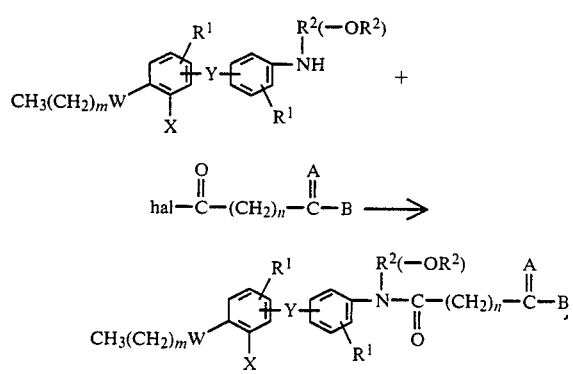

where X, W, Y, A, B, $R^1$ and $R^2$ and n are as defined hereinbefore and hal refers to a halo radical, for example, chloro or bromo. The reaction is carried out in an organic solvent, for instance tetrahydrofuran, and at reduced temperatures, with the reaction mixture being allowed to slowly warm to room temperature. Compounds in which Z is

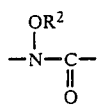

can be prepared in the exact same manner, except that the starting compound is an appropriate N-hydroxyaniline derivative instead of the aniline derivative.

Compounds in which the side chain Q is

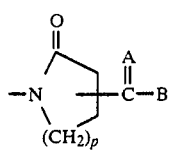

such as a 2-pyrrolidinone, can be prepared by reacting a suitable starting aniline derivative with, for example, a suitable itaconic acid as follows:

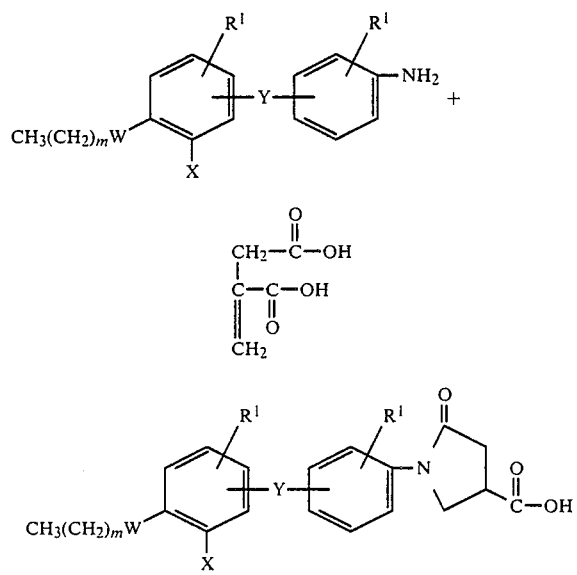

The starting aniline derivatives employed in reaction sequence can be prepared as in the following example:

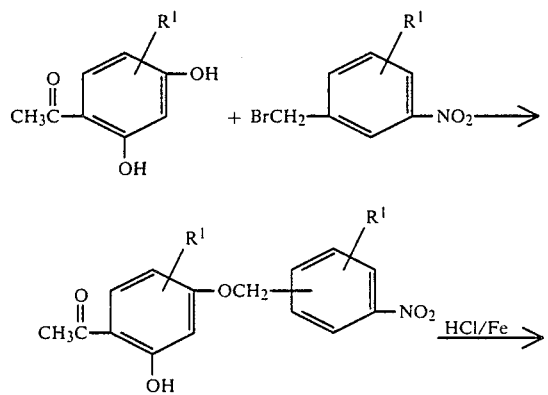

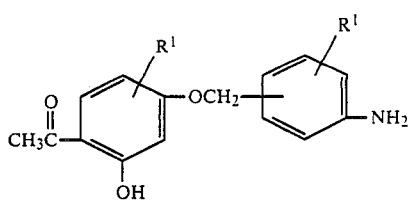

Compounds in which the bridge Y is —CH$_2$S— and —CH$_2$N— can be prepared in a like manner, using the appropriate nitrophenol or nitroaniline in place of the nitrophenol. Compounds in which the bridge Y is

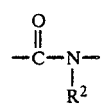

can be prepared by using the appropriate acyl chloride or acyl N-imidazole and the appropriate N-substituted nitroaniline. Finally, the starting N-hydroxyaniline derivatives can be prepared as follows:

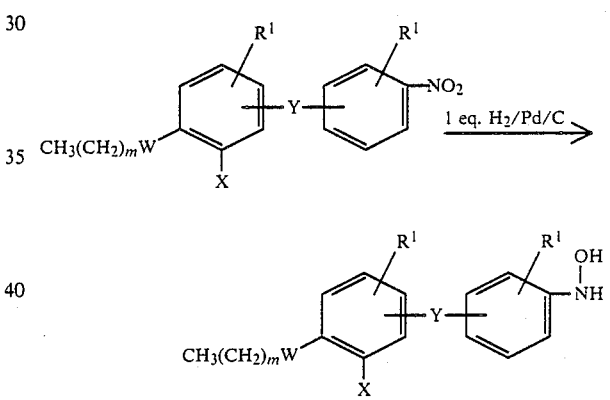

The starting carboxy or thiocarboxy alkanoyl derivative halides are commercially available or can be prepared by conventional methods.

The starting compounds for the preparation of compounds in which the linking bridge Y is —O—, —S— or

can be prepared by the following reaction sequence:

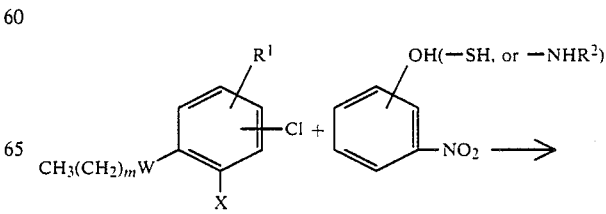

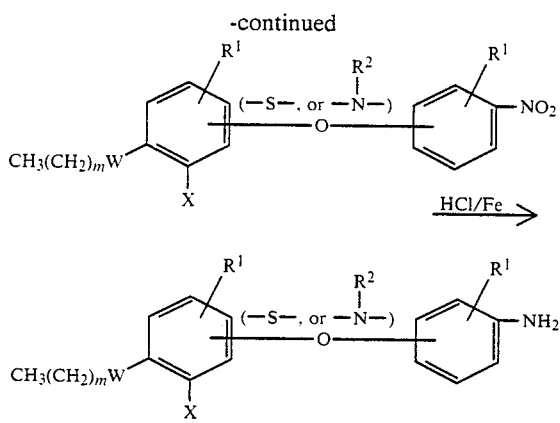

Compounds of the invention which contain a basic nitrogen are capable of forming pharmacologically acceptable salts, including the salts of pharmacologically acceptable organic and inorganic acids such as hydrochloric, hydrobromic, sulfuric, nitric, phosphoric, methanesulfonic, benzenesulfonic, acetic, citric, fumaric, maleic, succinic and the like. The compounds which are carboxylic acids or have a hydroxyamic function are capable of forming alkali metal and alkaline earth carboxylates and carboxylates of pharmacologically acceptable cations derived from ammonia or a basic amine. Examples of the latter include but are not limited to cations such as ammonium, mono-, di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl-piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

The compounds of the invention, by virtue of their ability to inhibit the activity of lipoxygenase enzyme and by their ability to anatagonize the effects of $LTD_4$ and $LTC_4$, which are the major constituents of SRS-A, are useful for the inhibition of symptoms induced by these leukotrienes. Accordingly, the compounds are indicated in the prevention and treatment of those disease states in which $LTD_4$ and $LTC_4$ are causative factors, for example allergic rhinitis, allergic bronchial asthma and other leukotriene mediated naso-bronchial obstructive air-passageway conditions, as well as in other immediate hypersensitivity reactions, such as allergic conjunctivitis. The compounds are especially valuable in the prevention and treatment of allergic bronchial asthma.

When the compounds of the invention are employed in the treatment of allergic airways disorders, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The lipoxygenase inhibitory and leukotriene antagonist effects of the compounds of the invention may be demonstrated by standard pharmacological procedures, which are described more fully in the examples given hereinafter.

These procedures illustrate the ability of the compounds of the invention to inhibit the polymorphonuclear leukocyte synthesis of the lipoxygenase products 5-HETE and 5,12-di-HETE; the ability of the compounds to antagonize $LTC_4$ and $LTD_4$-induced bronchospasm mediated by exogenously administered leukotrienes; and measure the in vivo activity of the compounds as lipoxygenase inhibitors and leukotriene antagonists of endogenous mediators of bronchospasm.

The following examples show the preparation and pharmacological testing of compounds within the invention.

EXAMPLE 1

3-[[3-[(4-acetyl-3-hydroxyphenoxy)methyl]phenyl]amino]-3-oxopropanoic acid, methyl ester

A.

3-[(4-acetyl-3-hydroxyphenoxy)methyl]nitrobenzene

A mixture of potassium carbonate (anhydrous, 31.7 g) and cesium carbonate (catalytic amount) is pulverized with mortar and pestle, then added to a solution of 2,4-dihydroxyacetophenone (35 g) in acetone (250 ml). The mixture is refluxed for 30 minutes. A solution of m-nitrobenzyl bromide (50 g) in acetone (100 ml) is added in one portion and the reaction refluxed for 3 days. After cooling to room temperature, water is added until a precipitate forms. The product is collected on a Buchner funnel, washed with water and ether. Recrystallization from acetone provides 36.9 g (56% yield) of needles, m.p. 117°–118° C.

B. 3-[(4-acetyl-3-hydroxyphenoxy)methyl]aniline

A mixture of 3-[(4-acetyl-3-hydroxyphenoxy)methyl]nitrobenzene (10.2 g) and iron powder (10.4 g) in ethanol (150 ml, saturated with anhydrous HCl) is stirred at room temperature for 15 hours. After removal of excess iron and concentration in vacuo, the residue is partitioned between dichloromethane and saturated sodium bicarbonate solution. The organic phase is filtered through a Florisil column with the aid of dichloromethane. Concentration gives 7.4 g of product (81% yield) m.p. 153°–154° C.

C.

3[[-[(4-acetyl-3-hydroxyphenoxy)methyl]phenyl]amino]-3-oxopropanoic acid, methyl ester A mixture of 3-[(4-acetyl-3-hydroxyphenoxy)methyl]aniline (3.3 g) and dimethyl malonate (50 ml) is heated in an oil bath at 140° C. for 2 hours. Excess malonate is removed in vacuo and the residue is dissolved in acetone. Storage at 0° C. gives crystalline product (4.1 g, 88%), m.p. 130°–132° C.

Analysis for: $C_{19}H_{19}NO_6$, Calculated: C, 63.86; H, 5.36; N, 3.92, Found: C, 63.55; H, 5.45; N, 3.71.

EXAMPLE 2

4-[[3-[(4-acetyl-3-hydroxyphenoxy)methyl]phenyl]amino]-4-oxobutanoic acid, methyl ester A solution of 3-[(4-acetyl-3-hydroxyphenoxy)methyl]aniline (3.4 g prepared as in Example 1B) and triethylamine (1.62 g) in tetrahydrofuran (40 ml) is cooled to −78° C. under nitrogen. To this solution is added 3-carbomethoxypropanoyl chloride (2 g, neat), dropwise. The reaction is left to warm to room temperature overnight, then poured onto 10% HCl and extracted with ether. The extracts are washed with saturated brine, and then dried over $MgSO_4$, and concentrated on a rotary evaporator. The residue is dissolved in a minimum amount of acetone, to which several drops of ether are added and then stored at 0° C. Filtration gives 2.6 g (53% yield) of product, m.p. 121°–123° C.

Analysis for: $C_{20}H_{21}NO_6$, Calculated: C, 64.88; H, 5.69; N, 3.77, Found: C, 64.87, H, 5.67; N, 3.93.

EXAMPLE 3

Following the procedure of Example 2, and using appropriate starting materials and reagents, the following compounds are prepared:
(a) 2-[[3-[(4-acetyl-3-hydroxyphenoxy)methyl]phenyl]amino]oxalic acid, methyl ester, m.p. 155°–157° C.
(b) 5-[[3-[(4-acetyl-3-hydroxyphenoxy)methyl]phenyl]-5-oxo-pentanoic acid, methyl ester, m.p. 110°–112° C.

EXAMPLE 4

3-[[3-[(4-acetyl-3-methoxyphenoxy)methyl]phenyl]amino]-3-oxopropanoic acid, methyl ester (A)
3-[(4-acetyl-3-methoxyphenoxy)methyl]nitrobenzene To a degreased suspension of sodium hydride (23 g) in tetrahydrofuran at ice temperature is slowly added (under nitrogen) a solution of 3-[(4-acetyl-3-hydroxyphenoxy)methyl]nitrobenzene (13.6 g, prepared as in Example 1A) in tetrahydrofuran (100 ml). When hydrogen evolution ceases, the mixture is allowed to warm to room temperature and is stirred for 2 hours. To this slurry is added iodomethane (6.7 g, neat) and the mixture is stirred 15 hours at room temperature. Another 6.7 g of iodomethane is then added and the mixture is refluxed 6 hours. After cooling to room temperature, the reaction mixture is poured into 10% HCl and extracted with ether. The extracts are washed with saturated brine, then dried over $MgSO_4$ and concentrated. Recrystallization from acetone gives 9.1 g (64% yield) of product, m.p. 111°–114° C.

(B) 3-[4-acetyl-3-methoxyphenoxy)methyl]aniline

The title compound is prepared using the procedure of Example 1B. From 7.6 g of 3-[(4-acetyl-3-methoxyphenoxy)methyl]nitrobenzene, 4.8 g (70% yield) of product is obtained, m.p. 116°–118° C.

(C)
3-[[3-[(4-acetyl-3-methoxyphenoxy)methyl]phenyl]amino]-3-oxopropanoic acid, methyl ester The title compound is prepared using the procedure of 1C, except that the crude product is boiled in ether and filtered to give a brown solid, m.p. 93.5°–96.5° C.

Analysis for: $C_{20}H_{21}NO_6$, Calculated: C, 64.68; H, 5.69; N, 3.77, Found: C, 65.05; H, 5.69; N, 3.55.

EXAMPLE 5

4-[[3-[(4-acetyl-3-methoxyphenoxy)methyl]phenyl]amino]-4-oxobutanoic acid, methyl ester The title compound is prepared as in Example 2, using the aniline of Example 4B and 3-carbomethoxypropanoyl chloride. The crude product is recrystallized from ether, m.p. 123.5°–124.5° C.

Analysis for: $C_{21}H_{23}NO_6 \cdot \frac{1}{4}H_2O$, Calculated: C, 64.69; H, 6.07; N, 3.59, Found: C, 64.62; H, 5.91; N, 3.36.

EXAMPLE 6

Following the procedures of Examples 1–5 and using the appropriate starting materials and reagents, the following compounds are prepared:
(a) 3-[[3-[[3-hydroxy-4-(1-oxohexyl)phenoxy]methyl]phenyl]amino]-3-oxopropanoic acid, methyl ester, m.p. 90°–91° C.
(b) 4-[[3-[[3-hydroxy-4-(1-oxohexyl)phenoxy]methyl]phenyl]amino]-4-oxobutanoic acid, methyl ester, m.p. 69°–70° C.
(c) 4-[[3-[[3-methoxy-4-(1-oxohexyl)phenoxy]methyl]phenyl]amino]-4-oxobutanoic acid, methyl ester, m.p. 103°–105° C.
(d) 3-[[3-[[3-methoxy-4-(1-oxohexyl)phenoxy]methyl]phenyl]amino]-3-oxopropanoic acid, methyl ester, m.p. 79°–81° C.

EXAMPLE 7

4-[[3-[(4-ethyl-3-methoxyphenoxy)methyl]phenyl]amino]-4-oxobutanoic acid, methyl ester (A) 3-[(4-ethyl-3-methoxyphenoxy)methyl]aniline Zinc dust (8.8 g) and mercuric chloride (0.7 g) are stirred in 25 ml of water for 10 minutes. The water is decanted and the amalgam is cooled in an ice bath as a solution of 3-[(4-acetyl-3-methoxy-phenoxy)methyl]nitrobenzene (4 g, prepared as in Example 3A) in ethanol (saturated with anhydrous HCl) is added cautiously. After addition is complete, the reaction mixture is refluxed overnight. After cooling to room temperature, the reaction mixture is poured into saturated sodium bicarbonate and extracted with dichloromethane. The extracts are dried over $MgSO_4$ and filtered through a column of Florisil. Concentration gives 2.9 g of product as a red-brown oil. The product is taken on to the next step without further purification.

(B)
4[[3-[(4-ethyl-3-methoxyphenoxy)methyl]phenyl]amino]-4-oxobutanoic acid, methyl ester The title compound is prepared as in Example 5 from the aniline of Example 7A above and 3-carbomethoxypropanoyl chloride. The crude oil is dissolved in acetone and stored at 0° C. The product separates as a white solid, m.p. 69°–70° C.

Analysis for: $C_{21}H_{25}NO_5$, Calculated: C, 67.91; H, 6.78; N, 3.77, Found: C, 67.57; H, 6.67; N, 3.6.

EXAMPLE 8

Following the procedures of Examples 4, 5 and 7 and using the appropriate reagents and starting materials, the following compounds are prepared:

(a) 3-[[3-[(4-ethyl-3-methoxyphenoxy)methyl]phenyl]amino]-3-oxopropanoic acid, methyl ester, m.p. 83°–85° C.

(b) 3-[[3-[(4-hexyl-3-methoxyphenoxy)methyl]phenyl]amino]-3-oxopropanoic acid, methyl ester, m.p. 73.5°–75.5° C.

(c) 4-[[3-[(4-hexyl-3-methoxyphenoxy)methyl]phenyl]amino]-4-oxobutanoic acid, methyl ester, m.p. 63°–65° C.

EXAMPLE 9

1-[[3-[(4-acetyl-3-hydroxyphenoxy)methyl]phenyl]-2-pyrrolidinone-4-carboxylic acid, methyl ester A mixture of itaconic acid (2.06 g) and 3-[(4-acetyl-3-hydroxyphenoxy)-methyl]aniline (3.67 g, prepared as in 1B) is heated (neat) in a 170° C. oil bath under nitrogen for 3 hours. The mixture is cooled to room temperature, methanol (20 cc) and p-toluene sulfonic acid (trace) are added, and the mixture is refluxed 15 hours. The methanol is removed in vacuo and the residue chromatographed on silica gel (elution with 1:1 hexane-ethyl acetate) to give 1.6 g of product, m.p. 111°–114° C.

Analysis for: $C_{21}H_{21}NO_6$, Calculated: C, 65.79; H, 5.52; N, 3.65, Found: C, 66.10; H, 5.59; N, 3.68.

EXAMPLE 10

4-[[3-[(4-acetyl-3-fluorophenoxy)methyl]phenyl]amino]-4-oxobutanoic acid, methyl ester (A) 3-[(4-acetyl-3-fluorophenoxy)methyl]nitrobenzene To a solution of 4-acetyl-3-fluorophenol (22.4 g) in acetone (100 ml) is added powdered potassium carbonate (anhydrous, 20 g) and cesium carbonate (catalytic amount). After 30 minutes of reflux, a solution of m-nitrobenzyl bromide (32.7 g) in acetone (100 ml) is added in one portion. The mixture is refluxed for 15 hours. Water is added to dissolve all solids followed by ether and saturated brine solution. The ether layer is dried over $MgSO_4$ and concentrated to an orange red oil. Addition of petroleum ether gives orange-yellow crystals (31 g, 74% yield), m.p. 92°–96° C.

The above starting material is prepared as follows:

To anhydrous zinc bromide (23 g) in ethylene dichloride (25 ml) at room temperature is added sequentially 3-fluorophenol (6.2 g) and acetyl chloride (4.8 g). After gas evolution ceases, the mixture is refluxed one week. The reaction mixture is cooled to room temperature and filtered through a short column of Florisil with the aid of dichloromethane. Concentration gives a red oil which solidifies upon addition of petroleum ether, m.p. 112°–116° C.

(B) 3-[(4-acetyl-3-fluorophenoxy)methyl]aniline

The title compound is prepared using the procedure of Example 1B. From 15 g of 3-[(4-acetyl-3-fluorophenoxy)methyl]nitrobenzene, 9.09 g (67% yield) of product is obtained, m.p. 85°–87° C.

(C)
4-[[3-[(4-acetyl-3-fluorophenoxy)methyl]phenyl]amino]-4-oxobutanoic acid, methyl ester The title compound is prepared according to the procedure of Example 2. From 2 g of 3-[(4-acetyl-3-fluorophenoxy)methyl]aniline and 3-carbomethoxypropanoyl chloride (1.39 g), 1.80 g (62% yield) of product is obtained after recrystallization from ethyl acetate-petroleum ether, m.p. 123°–126° C.

Analysis for: $C_{20}H_{20}NO_5F$, Calculated: C, 64.34; H, 5.39; N, 3.75, Found: C, 64.15; H, 5.42; N, 3.78.

EXAMPLE 11

Following the procedure of Example 10, and using the appropriate starting materials and reagents, the following compounds are prepared:

(a) 2-[[3-[(4-acetyl-3-fluorophenoxy)methyl]phenyl]amino]-oxalic acid, methyl ester, m.p. 141°–142° C.

(b) 5-[[3-[(4-acetyl-3-fluorophenoxy)methyl]phenyl]amino]-5-oxopentanoic acid, methyl ester, m.p. 104°–106° C.

EXAMPLE 12

1-[[3-[(4-acetyl-3-fluorophenoxy)methyl]phenyl]-2-pyrrolidinone-4-carboxylic acid, methyl ester The title compound is prepared using the procedure of Example 9. From 3.1 g of 3-[(4-acetyl-3-fluorophenoxy)methyl]aniline and 1.9 g of itaconic acid, 1.02 g of product is obtained from flash chromatography on silica gel (60 g., ethyl acetatehexane (1:1) elution), m.p. 88.5°–91.5° C.

Analysis for: $C_{21}H_{20}NO_5F$, Calculated: C, 65.45; H, 5.23; N, 3.63, Found: C, 65.25; H, 5.39; N, 3.69.

EXAMPLE 13

3-[[3-[(4-acetyl-3-fluorophenoxy)methyl]phenyl]amino]-3-oxopropanoic acid, methyl ester The title compound is prepared using the appropriate starting materials and the procedure of Example 1C. The crude product is chromatographed on silica gel (40 wt.eq.) with ethyl acetate-hexane (1:1) elution, m.p. 102°–104° C.

Analysis: $C_{19}H_{18}NO_5F \cdot \frac{1}{4}H_2O$, Calculated: C, 62.72; H, 5.12; N, 3.85, Found: C, 63.04; H, 5.09; N, 3.71.

EXAMPLE 14

The compounds 5- and 12-hydroxyeicosatetraenoic acid (5-HETE and 12-HETE) and 5,12-dihydroxyeicosatetraenoic acid (5,12-diHETE) are early arachidonic acid oxidation products in the lipoxygenase cascade, which have been shown to mediate several aspects of inflammatory and allergic response. This is especially true with respect to 5,12-diHETE, which is also denoted as $LTB_4$ [see Ford-Hitchinson, J. Roy. Soc. Med., 74, 831 (1981)]. The assay of this Example measures the ability of the compounds of the invention to inhibit the synthesis of 5-HETE and $LTB_4$ by rat glycogen-elicited polymorphonuclear leukocytes.

The assay is carried out as follows:

Peritoneal PMN are obtained from female Wistar rats (150–250 g) that received an i.p. injection of 6% glycogen (10 ml). After 24 hours, rats are killed by $CO_2$ asphyxiation and peritoneal cells are harvested by peritoneal lavage using $Ca^{++}$ and $Mg^{++}$ free Hanks' balanced salt solution (HBSS). The peritoneal exudate is centrifuged at 400 g for 10 minutes. After centrifugation, the lavaged fluid is removed and the cell pellet is resuspended in HBSS containing $Ca^{++}$ and $Mg^{++}$ and 10 mM L-cysteine at a concentration of $2 \times 10^7$ cells/ml. To 1 ml portions of cell suspension, test drugs or vehicle are added and incubated at 37° C. for 10 minutes. Following this preincubation, the calcium ionophore (10 $\mu M$), A23187, is added together with 0.5 $\mu Ci[^{14}C]$arachidonic acid and further incubated for 10 minutes. The reaction is stopped by the addition of ice cold water (3 ml) and acidifying to pH 3.5. Lipoxygenase products are then extracted twice into diethyl ether. The pooled ether extracts are evaporated to dryness under nitrogen and the residue is redissolved in a small volume of methanol and spotted on aluminum backed pre-coated thin layer chromatographic plates. The samples are then co-chromatographed with authentic reference 5-HETE, 12-HETE and 5,12-diHETE in the solvent system—hexane:ether:acetic acid (50:50:3). After chromatography, the areas associated with 5-HETE and 5,12-diHETE standards are identified by autoradiography, cut out and quantitated by liquid scintillation.

Results are expressed as % inhibition of $[^{14}C]$5-HETE and $[^{14}C]LTB_4$ (5,12-HETE)synthesis.

$$\% \text{ inhibition} = \frac{\text{control} - \text{test}}{\text{control}} \times 100$$

Testing compounds of the invention in this assay and using the antioxident 3-amino-1-[m-trifluoromethyl)-phenyl]-2-pyrazoline (BW755C) as a standard, the following results are obtained.

TABLE I

| Compound of Example Number | 50% Inhibitory Concentration ($IC_{50}$) $\mu m$ | |
|---|---|---|
| | 5-HETE | $LTB_4$ |
| BW755C | 43.00 | 30.00 |
| 1 | 14.20 | 11.70 |
| 2 | 20.80 | 27.80 |
| 4 | 12.10 | 19.90 |
| 5 | 36.30 | 34.70 |
| 6a | 3.44 | 4.14 |
| 6b | 2.01 | 2.24 |
| 6c | 3.71 | 3.87 |
| 6d | 2.73 | 3.14 |
| 7 | 5.60 | 7.09 |
| 8a | 4.54 | 5.50 |
| 8b | 1.59 | 1.70 |
| 8c | 1.08 | 1.33 |

The results show that compounds of this invention have significant activity in inhibiting the synthesis of the arachidonic acid lipoxygenase oxidation products 5-HETE and $LTB_4$.

EXAMPLE 15

The assay of this Example measures the in vivo ability of the compounds of the invention to inhibit the bronchospasm induced in guinea pigs by the exogenously administered leukotrienes $C_4$ and/or $D_4$. This assay is essentially a measure of the SRS-A antagonist properties of the compounds tested.

This assay is carried out as follows:

Male Hartley strain guinea pigs (350–600 g) are anesthetized with pentobarbital sodium (50 mg/kg, i.p.). The jugular vein is cannulated for injection of drugs and the carotid artery for monitoring blood pressure. The trachea is cannulated for artificial ventilation by a miniature Starling pump and for indirect measurement of respiratory volume changes as described infra. Additional pentobarbital sodium (15 mg/kg, i.v.) is administered to arrest spontaneous respiration. Submaximal bronchoconstrictor responses are established in control animals by varying the dose-levels of leukotriene. Intravenous dose-levels for $LTC_4$ range from 1 to 2 $\mu g/kg$ and for $LTD_4$ the range is from 0.3 to 1 $\mu g/kg$. The aerosol bronchoprovocation dose for $LTC_4$ is generated from 1.6 $\mu M$ solution and for $LTD_4$ from a 2.0 $\mu M$ solution.

Test drugs are administered either intravenously, intraduodenally, by aerosol or orally at 1 or 10 minutes before induction of bronchospasm by administration of either $LTC_4$ or $LTD_4$ at the predetermined dose-levels. Aerosols of soluble drugs or leukotrienes are produced in-line for 10 seconds only by actuation of an ultrasonic nebulizer (Monaghan). Aerosolized drug dosage is expressed in terms of solution concentration and by a fixed aerosol exposure time (approximately 10 seconds). Control animals receive saline in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at 1, 3 and 5 minutes are obtained from the recorded charts.

The overflow volume at 1, 3 and 5 minutes is expressed as a percentage of maximal bronchoconstriction. Combined group values are used from each of these time intervals to determine the inhibitory effect of drugs.

$$\% \text{ inhibition} = \frac{\% \text{ bronchoconstriction } (bc) \text{ in control group} - \% \text{ } bc \text{ in drug-treated groups}}{\% \text{ } bc \text{ in control group}} \times 100$$

Students t-test for unpaired data is used to determine statistical significance. Dose response curves are generated and $ED_{50}$ doses are interpolated from the regression lines.

Results for a compound of the invention in this assay, using $LTD_4$ for induction of bronchospasm, is given below:

TABLE II

| | Compound administered at 10 minutes before induction of bronchospasm | | | |
|---|---|---|---|---|
| Compound of Example Number | Dose mg/kg (Intraduodenal) | % Inhibition Overflow Volume at | | |
| | | 1 min. | 3 min. | 5 min. |
| 1 | 50 | 25 | 48 | 56 |

The results show that a representative compound of the invention has significant in vivo activity against $LTD_4$ induced bronchoconstriction.

EXAMPLE 16

The assay of this Example measures the in vivo ability of the compounds of the invention to inhibit the bronchospasm induced in guinea pigs by endogenous mediators of the bronchoconstriction.

The assay is carried out as follows:

Male Hartley strain guinea pigs weighing 350-600 g are sensitized to ovalbumin (OA) (5 mg i.p. and 5 mg s.c.) on day 0. Three to five weeks later, the animals are anesthetized with pentobarbital sodium (50 mg/kg, i.p.). The jugular vein is cannulated for injection of drugs and the carotid artery for monitoring blood pressure. The trachea is cannulated for artificial ventilation by miniature Staring pump and for indirect measurement of respiratory volume changes as described, infra. Additional pentobarbital sodium (15 mg/kg, i.v.) is administered to arrest spontaneous respiration. A cyclooxygenase inhibitor, indomethacin (10 mg/kg in tris buffer, i.v. at 9 min.) is administered to shunt arachidonic metabolism to lipoxygenase pathways. One minute later, chlorpheniramine (1.0 mg/kg in saline, i.v.) is given to attenuate the histaminic component of anaphylactic bronchoconstriction. Test drugs are administered either intravenously, intraduodenally or by aerosol at 2 or 10 minutes before antigen challenge. Anaphylactic bronchoconstriction is induced by administration of aerosolized OA (1%). Aerosols of OA or soluble drug are produced in-line for 10 seconds only by actuation of an ultrasonic nebulizer (Monaghan). Aerosolized drug dosage is expressed in terms of solution concentration and by a fixed aerosol exposure time (approximately 10 seconds). Control animals receive saline in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at minutes 1, 3 and 5 are obtained from the recorded charts.

The overflow volume at 1, 3 and 5 minutes is expressed as a percentage of maximal bronchoconstriction. Combined group values are used from each of these time intervals to determine the inhibitory effect of drugs.

$$\% \text{ inhibition} = \frac{\% \text{ bronchoconstriction } (bc) \text{ in control group} - \% bc \text{ in drug-treated groups}}{\% bc \text{ in control group}} \times 100$$

Students t-test for unpaired data is used to determine statistical significance. Dose response curves are generated and $ED_{50}$ doses are interpolated from the regression lines.

The results for three compounds of the invention, with administration of the compounds at 10 minutes before ovalbumin challenge are presented below:

TABLE III

| Compound of Example Number | Dose mg/kg (Intraduodenal) | % Inhibition Overflow Volume at | | |
|---|---|---|---|---|
| | | 1 min. | 3 min. | 5 min. |
| 1 | 50 | 99 | 77 | 63 |
| 2 | 50 | 93 | 24 | 35 |
| 4 | 50 | 88 | 67 | 46 |

The results show that compounds of the invention have significant in vivo activity in inhibiting ovalbumin induced bronchospasm mediated by endogenous products of the lipoxygenase oxidation of arachidonic acid.

What is claimed is:

1. A compound having the formula

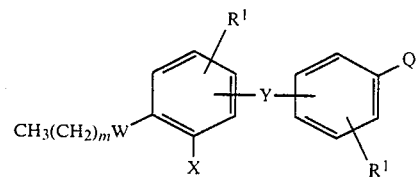

wherein
X is $OR^2, SR^2, N(R^2)_2$ or halo;
W is

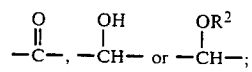

Y is $-CH_2O-$, $-OCH_2-$, $-CH_2S-$, $-SCH_2-$,

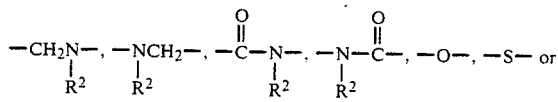

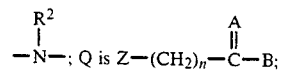

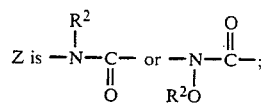

m is 0-6;
n is 0-6;
p is 1-3;
A is O or S;
B is $OR^2, SR^2$ or $N(R^2)_2$;
$R^1$ is hydrogen, loweralkyl, loweralkoxy or halo;
$R^2$ is hydrogen or loweralkyl;
and the pharmaceutically acceptable salts thereof.

2. The compound of claim 1, which is 3-[[3-[(4-acetyl-3-hydroxyphenoxy)methyl]phenyl]amino]-3-oxopropanoic acid, methyl ester.

3. The compound of claim 1, which is 4-[[3-[(4-acetyl-3-hydroxyphenoxy)methyl]phenyl]amino]-4-oxobutanoic acid, methyl ester.

4. The compound of claim 1 which is 2-[[3-[(4-acetyl-3-hydroxyphenoxy)methyl]phenyl]amino]oxalic acid, methyl ester.

5. The compound of claim 1, which is 5-[[3-[(4-acetyl-3-hydroxyphenoxy)methyl]phenyl]-5-oxo-pentanoic acid, methyl ester.

6. The compound of claim 1, which is 3-[[3-[(4-acetyl-3-methoxyphenoxy)methyl]phenyl]amino]-3-oxopropanoic acid, methyl ester.

7. The compound of claim 1, which is 4-[[3-[(4-acetyl-3-methoxy-phenoxy)methyl]phenyl]amino]-4-oxobutanoic acid, methyl ester.

8. The compound of claim 1, which is 3-[[3-[[3-hydroxy-4-(1-oxohexyl)phenoxy]methyl]phenyl]amino]-3-oxopropanoic acid, methyl ester.

9. The compound of claim 1, which is 4-[3-[[3-hydroxy-4-(1-oxohexyl)phenoxy]methyl]phenyl]amino]-4-oxobutanoic acid, methyl ester.

10. The compound of claim 1, which is 4-[[3-[[3-methoxy-4-(1-oxohexyl)phenoxy]methyl]phenyl]amino]-4-oxobutanoic acid, methyl ester.

11. The compound of claim 1, which is 3-[[3-[[3-methoxy-4-(1-oxohexyl)phenoxy]methyl]phenyl]amino]-3-oxopropanoic acid, methyl ester.

12. The compound of claim 1, which is 4-[[3-[(4-acetyl-3-fluorophenoxy)methyl]phenyl]amino]-4-oxobutanoic acid, methyl ester.

13. The compound of claim 1, which is 2-[[3-[(4-acetyl-3-fluorophenoxy)methyl]phenyl]amino]-oxalic acid, methyl ester.

14. The compound of claim 1, which is 5-[[3-[(4-acetyl-3-fluorophenoxy)methyl]phenyl]amino]-5-oxopentanoic acid, methyl ester.

15. The compound of claim 1, which is 3-[[3-[(4-acetyl-3-fluorophenoxy)methyl]phenyl]amino]-3-oxopropanoic acid, methyl ester.

16. The compound 3-[[3-[(4-hexyl-3-methoxyphenoxy)methyl]phenyl]amino]-3-oxopropanoic acid, methyl ester.

17. The compound 4-[[3-[(4-hexyl-3-methoxyphenoxy)methyl]phenyl]amino]-4-oxobutanoic acid, methyl ester.

* * * * *